United States Patent
Yamada et al.

(10) Patent No.: US 10,466,104 B2
(45) Date of Patent: Nov. 5, 2019

(54) MASS SPECTROMETRIC DATA ANALYZER AND PROGRAM FOR ANALYZING MASS SPECTROMETRIC DATA

(71) Applicant: SHIMADZU CORPORATION, Kyoto-shi, Kyoto (JP)

(72) Inventors: Yosihiro Yamada, Kyoto (JP); Hiroto Tamura, Nagoya (JP); Teruyo Kato, Nagoya (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 0 days.

(21) Appl. No.: 15/986,306

(22) Filed: May 22, 2018

(65) Prior Publication Data

US 2018/0340827 A1 Nov. 29, 2018

(30) Foreign Application Priority Data

May 23, 2017 (JP) .................. 2017-101557

(51) Int. Cl.
*G01J 3/28* (2006.01)
*G06F 17/18* (2006.01)
(Continued)

(52) U.S. Cl.
CPC ............. *G01J 3/28* (2013.01); *C12Q 1/689* (2013.01); *C12Q 1/6895* (2013.01); *G06F 17/18* (2013.01);
(Continued)

(58) Field of Classification Search
CPC ............. G01J 3/28; G01J 2003/2859; G01J 2003/2866; C12Q 1/689; C12Q 1/6895;
(Continued)

(56) References Cited

U.S. PATENT DOCUMENTS

| 2004/0195500 A1* | 10/2004 | Sachs | G06F 19/24 250/282 |
| 2010/0286927 A1* | 11/2010 | Horn | H01J 9/0045 702/19 |

(Continued)

FOREIGN PATENT DOCUMENTS

JP     5750676 B2     7/2015

OTHER PUBLICATIONS

"Mass++ Beginners' Guide", XP055515175, May 15, 2014 (115 pages) Retrieved from the Internet: URL:https://www.shimadzu.co.jp/aboutus/ms_r/n00kbc0000006dat-att/MassBeginners_en.pdf [retrieved on Oct. 15, 2018].

(Continued)

*Primary Examiner* — Nicole M Ippolito
(74) *Attorney, Agent, or Firm* — Sughrue Mion, PLLC

(57) ABSTRACT

[Problem to be Solved]
To select a marker peak which characterizes a difference between groups, even when the number of samples belonging to each group is small.
[Solution]
A peak matrix is created based on the peaks detected from mass spectra of a plurality of samples belonging to a plurality of groups (S1-S3). Each row of the peak matrix represents a peak-intensity distribution for a large number of samples at one mass-to-charge-ratio value. If there is no difference between the groups at a certain mass-to-charge-ratio value, the peak-intensity distribution at that mass-to-charge-ratio value should be a lognormal distribution (or normal distribution). Accordingly, a hypothesis test for the conformity of the peak-intensity distribution to the lognormal distribution is performed for each mass-to-charge-ratio
(Continued)

value (S5). A mass-to-charge-ratio value at which a significant difference has been found is selected as a candidate of the marker peak (S6).

10 Claims, 8 Drawing Sheets

(51) Int. Cl.
  *H01J 49/26* (2006.01)
  *H01J 49/02* (2006.01)
  *C12Q 1/689* (2018.01)
  *C12Q 1/6895* (2018.01)
  *H01J 49/00* (2006.01)

(52) U.S. Cl.
  CPC ........ *H01J 49/0036* (2013.01); *H01J 49/025* (2013.01); *H01J 49/26* (2013.01); *C12Q 2600/158* (2013.01); *G01J 2003/2859* (2013.01); *G01J 2003/2866* (2013.01)

(58) Field of Classification Search
  CPC ............... C12Q 2600/158; G06F 17/18; H01J 49/0036; H01J 49/025; H01J 49/26
  USPC .................................................. 250/281, 282
  See application file for complete search history.

(56) References Cited

U.S. PATENT DOCUMENTS

| | | | |
|---|---|---|---|
| 2010/0299076 A1* | 11/2010 | Kajihara | G01N 33/6848 702/19 |
| 2014/0129169 A1* | 5/2014 | Noda | G01N 30/8665 702/89 |
| 2016/0148791 A1 | 5/2016 | Bloomfield et al. | |
| 2018/0000963 A1* | 1/2018 | Chao | C07K 16/3023 |

OTHER PUBLICATIONS

Communication dated Oct. 23, 2018, from European Patent Office in counterpart application No. 18173592.9.

"AXIMA Biseibustu Doutei Shisutemu (AXIMA microorganisms identification system)", Shimadzu Corporation, <URL:http://www.an.shimadzu.co.jp/ms/axima/mis.htm> and <URL:https://www.ssi.shimadzu.com/products/maldi-tofmass-spectrometry/id-plus.html>.

S. Kabuki et al., "Development of an atmospheric Cherenkov imaging camera for the CANGAROO-III experiment", Proceedings of the Universe Viewed in Gamma-rays, University of Tokyo Workshop 2002, Sep. 25-28, 2002, 9 pages.

H.W. Lilliefors, "On the Kolmogorov-Smirnov Test for Normality with Mean and Variance Unknown", Journal of the American Statistical Association, Jun. 1967, pp. 399-402, vol. 62, No. 399-402.

* cited by examiner

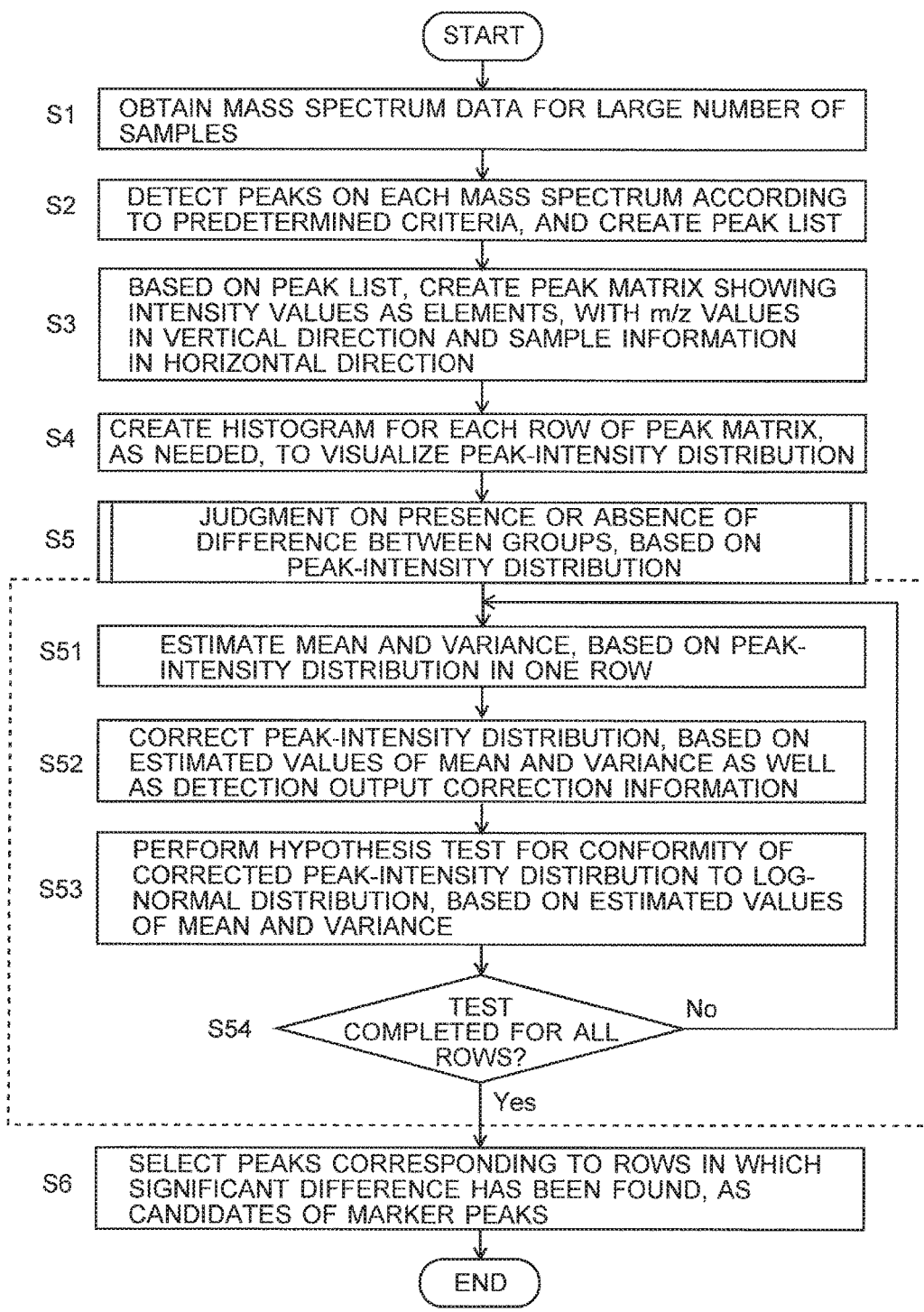

CONCEPT OF PEAK MATRIX

EXAMPLE OF PEAK MATRIX

|  | Group01 | | | | Group02 | | | |
| --- | --- | --- | --- | --- | --- | --- | --- | --- |
| m/z | Sample 01-1 | Sample 01-2 | Sample 01-3 | Sample 01-4 | Sample 02-1 | Sample 02-2 | Sample 02-3 | Sample 02-4 |
| 200.21 | 3.51E+05 | 3.54E+05 | 3.22E+04 | 2.76E+04 | 1.84E+04 | 1.85E+04 | 4.69E+04 | 3.36E+04 |
| 2010.4 | 4.12E+04 | 6.44E+04 | 3.55E+04 | 1.36E+05 | 1.03E+04 | 1.13E+04 | 3.93E+04 | 1.60E+04 |
| 2023.49 | 2.55E+05 | 2.52E+05 | 2.54E+04 | 0 | 7.45E+05 | 0 | 4.26E+05 | 7.63E+05 |
| 2043.74 | 5.99E+04 | 7.41E+04 | 4.23E+04 | 1.93E+04 | 4.50E+04 | 6.98E+04 | 3.03E+04 | 3.57E+04 |
| 2070.17 | 1.42E+04 | 5.44E+04 | 1.74E+04 | 3.66E+03 | 1.90E+05 | 3.58E+05 | 1.56E+05 | 3.47E+05 |
| ... | | | | | | | | |

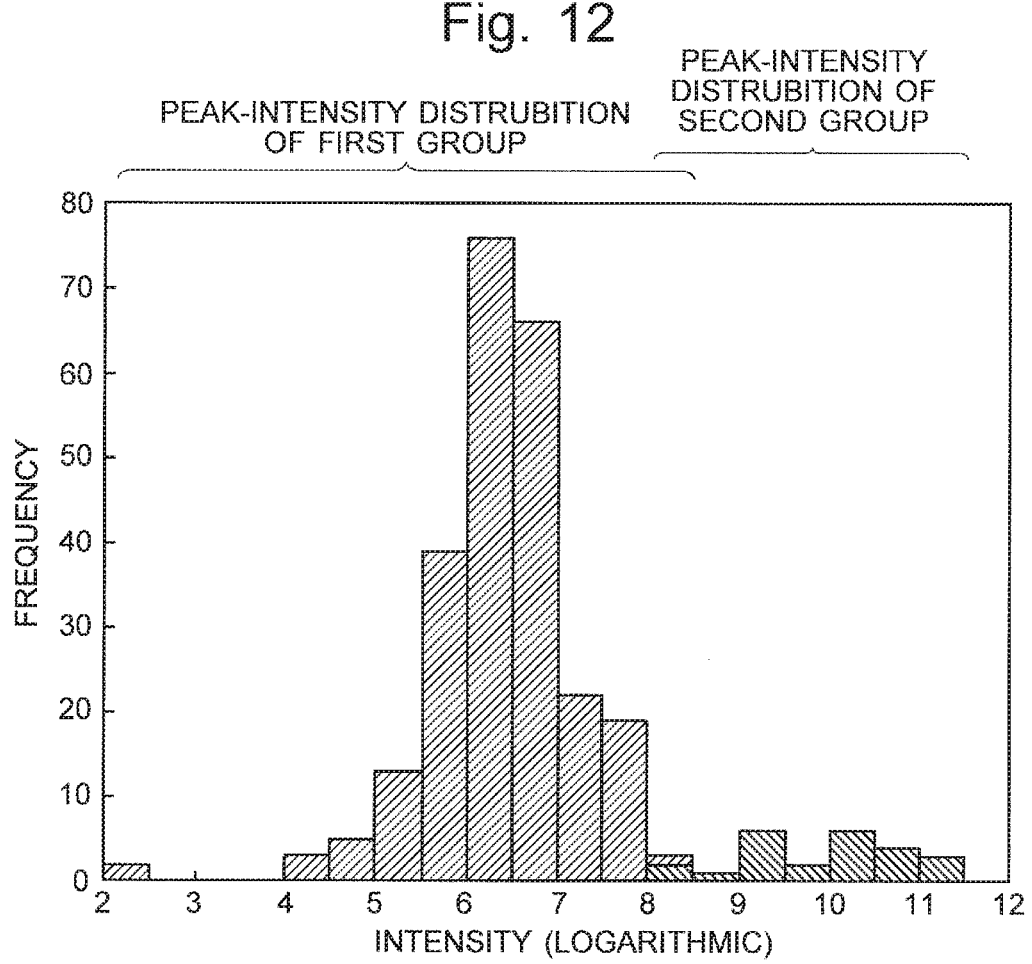

MASS SPECTROMETRIC DATA ANALYZER AND PROGRAM FOR ANALYZING MASS SPECTROMETRIC DATA

TECHNICAL FIELD

The present invention relates to a mass spectrometric data analyzer for analytically processing mass spectrum data obtained by performing mass spectrometric analyses as well as a computer program for such a data analyzer. More specifically, it relates to a mass spectrometric data analyzer and computer program suitable for performing a difference analysis among a plurality of sample groups.

BACKGROUND ART

In recent years, the method of identifying microorganisms (bacteria and fungi) using matrix-assisted laser desorption/ionization time-of-flight mass spectrometer (MALDI-TOF MS) has been rapidly spread due to its economic efficiency and analytic speediness (for example, see Non Patent Literature 1 or Patent Literature 1). In particular, identifying microorganisms at the level of species or lower levels (e.g. strains) allows for the acquisition of information that is extremely useful in medical areas, e.g. for assessing the pathogenicity of microorganisms or identifying the source of infection. For such analyses, it is necessary to find a "biomarker", i.e. a mass spectrum peak whose expression varies among microorganisms each of which belongs to a different group. In the following descriptions, a biomarker is simply called a "marker", and a peak which can be used as a marker on mass spectra is called a "marker peak".

To find a marker peak, it is normally necessary to perform a measurement using a mass spectrometer for each of the samples respectively derived from a plurality of groups, and perform a difference analysis of the obtained data for statistically analyzing the difference in peak intensity between the groups. An outline of a conventionally and commonly known procedure to search for a marker peak for identifying microorganisms using a difference analysis is as follows.

[Step A1] Samples are prepared in such a manner that each of which belongs to one of a plurality of groups that differ from each other in terms of the species/strain of fungi or culture conditions, with each group including $N_g$ samples. The total number of groups is $N_G$. The total number of samples is $N_s$.

[Step A2] A mass spectrum is acquired for each sample by performing a mass spectrometric analysis for the sample. The total number of mass spectra is the same as that of the samples, $N_s$.

[Step A3] A peak detection is performed for each of the $N_s$ mass spectra to collect peak information, i.e. the mass-to-charge-ratio value and signal-intensity value of each peak. Then, for each sample, the peak information of the sample is organized into a peak list. A peak list is a collection of mass-to-charge-ratio values and corresponding signal-intensity values of the peaks sorted by mass-to-charge-ratio value. The total number of peak lists is also $N_s$.

[Step A4] Using one peak list corresponding to one sample as one column vector, a peak matrix $M_p$ is created by arranging the peak lists as the column vectors in the row direction, i.e. in the horizontal direction, in such a manner that the signal-intensity values corresponding to the same mass-to-charge-ratio value are arrayed in the same row. In this peak matrix, the peak lists are sorted by group. The number of columns of the created peak matrix $M_p$ is the same as the total number of samples, $N_s$. The number of rows is equal to the total number of peaks observed for all samples, $N_p$ (it should be noted that two or more peaks whose mass-to-charge-ratio values fall within a specific threshold are considered as the same peak and counted as one peak). FIG. 3B shows one example of the peak matrix.

[Step A5] Each row of the peak matrix $M_p$ contains $N_s$ signal-intensity values. Each of those values belongs to one of the $N_G$ groups. A univariate analysis is performed on those signal-intensity values to analyze whether or not there is a difference between the groups and calculate a p-value for each row. For the univariate analysis, the t-test or U test is popularly used for $N_G=2$, while ANOVA is popularly used for $N_G \geq 3$.

[Step A6] The p-values calculated in Step A5 are each compared with a previously determined significance level a to select a row (i.e. peak) which shows a significant difference. Each peak corresponding to a row which shows a significant difference is listed as a candidate of the marker peak.

Candidates of the marker peaks are subjected to further selections from other points of view unrelated to mass spectrometry, or more specifically, through the consideration of biological mechanisms, validity check based on additional experiments, or other processes. Each candidate having sufficient grounds for selection is judged to be a marker peak.

CITATION LIST

Patent Literature

Patent Literature 1: JP 5750676 B

Non Patent Literature

Non Patent Literature 1: "AXIMA Biseibustu Doutei Shisutemu (AXIMA microorganisms identification system)", Shimadzu Corporation, [online], [accessed on Apr. 11, 2017], the Internet.

Non Patent Literature 2: S. Kabuki and five other authors, "Development of an atmospheric Cherenkov imaging camera for the CANGAROO-III experiment", *Proceedings of The Universe Viewed in Gamma-rays*, University of Tokyo Workshop 2002, Sep. 25-28, 2002

Non Patent Literature 3: Lilliefors H. W., "On the Kolmogorov-Smirnov Test for Normality with Mean and Variance Unknown", *Journal of the American Statistical Association*, Vol. 62, No. 318, 1967, pp. 399-402

SUMMARY OF INVENTION

Technical Problem

To perform a difference analysis by the previously described procedure, it is necessary to prepare a sufficient number of samples for each group and perform a mass spectrometric analysis on each sample. If there are many groups, operators will be considerably burdened with sample preparations, such as the culturing and pretreatments. The task of performing a mass spectrometric analysis on each sample will also be extremely complex and time-consuming.

The present invention has been developed to solve the previously described problem. Its primary objective is to provide a mass spectrometric data analyzer as well as a program for analyzing mass spectrometric data with which a peak that shows a difference between groups of samples (marker peak) can be located with a high degree of certainty even when the number of groups is large while the number of samples per one group is comparatively small.

Solution to Problem

The mass spectrometric data analyzer according to the present invention developed for solving the previously described problem is a mass spectrometric data analyzer for locating a marker peak whose expression varies among a plurality of groups of samples, based on mass spectrum data obtained by performing a mass spectrometric analysis on each of the samples each of which belongs to one of the plurality of groups, the mass spectrometric data analyzer including:

a) a peak information collector for grouping peak-intensity values on mass spectra obtained for a plurality of given samples, for each mass-to-charge-ratio value at which a peak is observed on any one of the mass spectra, based on mass spectrum data obtained for the given samples; and b) a significant difference determiner for determining, for each mass-to-charge-ratio value, whether or not a peak-intensity distribution is in conformity to a probability distribution using a predetermined parameter, the peak-intensity distribution being either a distribution based on a plurality of peak-intensity values corresponding to one mass-to-charge-ratio value, determined by the peak information collector, or a distribution obtained by correcting the aforementioned distribution, and for selecting a mass-to-charge-ratio value giving a peak-intensity distribution which is judged to be in inconformity to the probability distribution, as a candidate of a marker peak which is considered as showing a significant difference between the plurality of groups.

The program for analyzing mass spectrometric data according to the present invention developed for solving the previously described problem is a program for analyzing mass spectrometric data using a computer, to locate a marker peak whose expression varies among a plurality of groups of samples, based on mass spectrum data obtained by performing a mass spectrometric analysis on each of the samples each of which belongs to one of the plurality of groups. The program makes the computer perform the following steps:

a) a peak information collection step in which peak-intensity values on mass spectra obtained for a plurality of given samples are grouped for each mass-to-charge-ratio value at which a peak is observed on any one of the mass spectra, based on mass spectrum data obtained for the given samples; and b) a significant difference determination step in which, for each mass-to-charge-ratio value, whether or not a peak-intensity distribution is in conformity to a probability distribution using a predetermined parameter is determined, the peak-intensity distribution being either a distribution based on a plurality of peak-intensity values corresponding to one mass-to-charge-ratio value, determined in the peak information collection step, or a distribution obtained by correcting the aforementioned distribution, and a mass-to-charge-ratio value giving a peak-intensity distribution which is judged to be in inconformity to the probability distribution is selected as a candidate of a marker peak which is considered as showing a significant difference between the plurality of groups.

In the mass spectrometric data analyzer and program for analyzing mass spectrometric data according to the present invention, the samples to be subjected to a mass spectrometric analysis are, for example, living organisms or samples of biological origin. Typical examples are microorganisms, such as bacteria.

For example, in a situation in which one kind of ion originating from one compound arrives at a detector in a time-of-flight mass spectrometer, the temporal change in the number of ions arriving at the detector (i.e. the change in the ion intensity at a specific mass-to-charge-ration value) is expected to be in conformity to a normal distribution (in a strict sense, the arrivals of ions are discrete events and should be expressed by a Poison distribution, although the number of ions is normally so large that it is acceptable to consider the number of ions as a continuous quantity). In this case, it is possible to expect that a peak-intensity distribution (in the present description, a "frequency distribution of peak-intensity values" is called a "peak-intensity distribution") for one kind of ion originating from one compound, obtained from mass spectra corresponding to a large number of samples having the same nature or characteristics, is also in conformity to a normal distribution. As another example, it is often the case that a secondary electron multiplier, microchannel plate or similar detector having exponential amplification characteristics is used as a detector in a mass spectrometer. In such a case, it is possible to consider that the peak-intensity distribution will be in conformity to a lognormal distribution rather than an ordinary normal distribution.

In other words, if the peak-intensity distribution of a certain ion is not in conformity to a normal distribution or lognormal distribution, it is possible to consider that it is likely that the large number of original samples do not have the same nature or characteristics. That is to say, it is likely that those samples do not belong to one group having the same nature or characteristics. Based on such a basic idea, the mass spectrometric data analyzer and program for analyzing mass spectrometry data according to the present invention determine, for each mass-to-charge ratio, whether or not a plurality of samples can be considered as belonging to the same group, to locate a marker peak that is useful for dividing a large number of samples into a plurality of groups which differ from each other in nature or characteristics.

In the mass spectrometric data analyzer according to the present invention, when mass spectrum data of a plurality of samples each of which belongs to one of the plurality of groups are given, the peak information collector analyzes the mass spectrum data to locate each mass-to-charge ratio at which a peak is observed on at least one of the mass spectra and collect information concerning the peak-intensity values on the mass spectra for each of the located mass-to-charge ratios. A plurality of peak-intensity values (in practice, a considerably large number of peak-intensity values) corresponding to one mass-to-charge-ratio value form a peak-intensity distribution. Accordingly, for each peak-intensity distribution at a different mass-to-charge-ratio value, the significance difference determiner determines whether or not the distribution is in conformity to a normal distribution or lognormal distribution, for example. If a peak-intensity distribution has been judged to be in conformity to a normal distribution or lognormal distribution, it is concluded that there is no difference between the groups. If a peak-intensity distribution has been judged to be in inconformity to a normal distribution or lognormal distribution, it is concluded that there is a difference between the groups. A mass-to-charge-ratio value which gives such a peak-intensity distribution is selected as a candidate of the marker peak.

In the conventional analyzing technique described earlier, the determination on whether or not there is a difference between groups is made by determining whether or not there is a significant difference in a certain value (e.g. mean value) calculated from the result of an analysis on samples belonging to each group. Therefore, there is the tendency that, when the number of samples belonging to one group is small, the analysis result obtained for one sample has a significant influence, and a false-positive determination on the presence of the difference between the groups is more likely to be made when there is actually no such difference. By comparison, in the mass spectrometric data analyzer according to the present invention, analysis results obtained for samples belonging to a plurality of groups are collectively analyzed in the form of a peak-intensity distribution. Therefore, even when the number of samples belonging to one group is small, the influence of an analysis result of one sample is less likely to be reflected. Consequently, the determination on the presence or absence of the difference between the groups can be made with high accuracy even when the number of samples belonging to one group is small.

In a preferable configuration of the mass spectrometric data analyzer according to the present invention, the probability distribution is a normal distribution or lognormal distribution, and the significant difference determiner includes:

b1) a mean-and-variance estimator for estimating a mean and a variance from an uncorrected or corrected peak-intensity distribution; and b2) a statistical tester for performing a hypothesis test for the conformity of the uncorrected or corrected peak-intensity distribution to the normal distribution or lognormal distribution, based on the mean and the variance estimated by the mean-and-variance estimator.

The method for the hypothesis test is not specifically limited. A hypothesis test yields a p-value as its output, and this p-value can be compared with an appropriate significance level to determine whether or not the hypothesis should be rejected. According to this configuration, it is possible to correctly and efficiently determine whether or not a peak-intensity distribution is in conformity to a normal distribution or lognormal distribution.

In the previously described configuration of the mass spectrometric data analyzer according to the present invention, the significant difference determiner may further include a saturation characteristics corrector for correcting the peak-intensity distribution to remove an influence of output saturation characteristics of a detector in a mass spectrometer, and determine whether or not the peak-intensity distribution after correction by the saturation characteristics corrector is in conformity to the normal distribution of lognormal distribution.

According to this configuration, even in the case where the phenomenon that the output of the detector in the mass spectrometer becomes saturated with an increase in the actual signal intensity occurs, the influence of the saturation can be removed or reduced, and whether or not there is a difference between the groups can be correctly determined.

The saturation characteristics corrector may be configured to correct the peak-intensity distribution using an inverse function of a previously determined detector characteristics function. Typically, the detector characteristics function can be determined, for example, by the manufacturer of the device by actual measurements.

As one mode of the mass spectrometric data analyzer according to the present invention, the peak information collector may include:

a1) a peak detector for detecting a peak on each of given mass spectra obtained for a plurality of samples; and a2) a peak matrix creator for creating a peak matrix based on information concerning the peaks detected in each mass spectrum, the peak matrix including peak-intensity values arrayed as elements, with the mass-to-charge-ratio values of the peaks assigned to columns or rows, and information for identifying the samples assigned to rows or columns, and the significant difference determiner creates a peak-intensity distribution for each row or column in which peak-intensity values corresponding to the same mass-to-charge-ratio value are arrayed in the peak matrix.

In this configuration, a peak matrix containing an exhaustive and complete set of peak information related to the samples is created. Therefore, it is possible to assuredly make a judgment on the peak-intensity distribution for every mass-to-charge ratio at which a peak is located.

To visualize the peak-intensity distribution at each mass-to-charge-ratio value, the mass spectrometric data analyzer according to the present invention may have the function of creating a histogram which shows the relationship between the class and frequency of the peak-intensity values at each mass-to-charge-ratio value, and displaying or printing out the histogram according to an order from a user.

Advantageous Effects of the Invention

In the mass spectrometric data analyzer and program for analyzing mass spectrometric data according to the present invention, when a search is made for a marker peak which shows a significant difference between a plurality of groups each of which includes a plurality of samples as its members, the marker peak can be located with a high degree of certainty even when the number of samples per one group is comparatively small. This allows for a smaller number of samples to be prepared for each group for a difference analysis, so that the burden on operators in preparing samples will be reduced. The cost for the sample preparation will also be decreased. Furthermore, since the total number of samples to be subjected to mass spectrometry also decreases, the time required for the analysis will be shortened, so that the identification of microorganisms or similar tasks can be efficiently performed.

BRIEF DESCRIPTION OF DRAWINGS

FIG. 2 is a flowchart of a marker peak candidate selection process in the mass spectrometer system according to the embodiment.

FIG. 12 is a histogram of the intensity distribution of each peak in the case where the entire distribution is supposed to be a superposition of two peak-intensity distributions.

DESCRIPTION OF EMBODIMENTS

Figure 1:
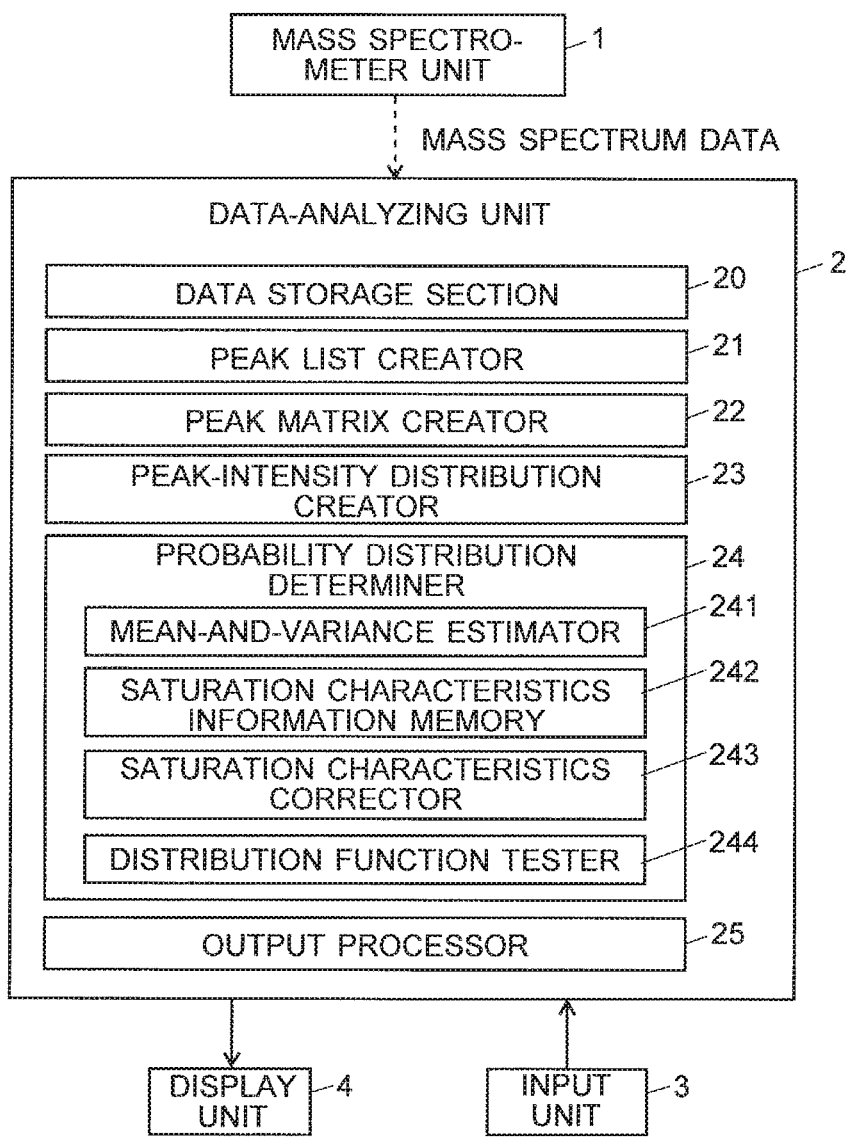
FIG. 1 is a schematic block configuration diagram of one embodiment of a mass spectrometer system including a mass spectrometric data analyzer according to the present invention.

One embodiment of the mass spectrometric data analyzer according to the present invention is hereinafter described with reference to the attached to drawings. FIG. 1 is a schematic block configuration diagram of one embodiment of a mass spectrometer system including a mass spectrometric data analyzer according to the present invention.

The mass spectrometer system according to the present embodiment includes a mass spectrometer unit 1, data-analyzing unit 2, input unit 3 and display unit 4. The mass spectrometer unit 1 in the present embodiment is a matrix-assisted laser desorption/ionization time-of-flight mass spectrometer (MALDI-TOF MS), which includes a MALDI ion source, time-of-flight mass separator and detector. The detector is a detector employing a multi-dynode secondary electron multiplier or microchannel plate, both of which have exponential amplification characteristics.

The data-analyzing unit 2 includes a data storage section 20, peak list creator 21, peak matrix creator 22, peak-intensity distribution creator 23, probability distribution determiner 24, and output processor 25 as its functional blocks. The probability distribution determiner 24 includes a mean-and-variance estimator 241, saturation characteristics information memory 242, saturation characteristics corrector 243 and distribution function tester 244.

Typically, the actual form of the data-processing unit 2 is a personal computer or more sophisticated computer, such as a workstation. Dedicated data-analyzing software is installed on the computer. The aforementioned functional blocks are embodied by executing this software on the same computer. In such a configuration, the data-analyzing software installed on the computer corresponds to the program for analyzing mass spectrometric data according to the present invention.

The procedure of the difference analysis in the mass spectrometer system according to the present embodiment is hereinafter described with reference to FIG. 2. FIG. 2 is a flowchart of a marker peak candidate selection process in the mass spectrometer system according to the present embodiment. The following description deals with the case of performing a process of locating a marker peak (i.e. a mass-to-charge-ratio value to be used as a marker) whose expression varies among a plurality of different groups (e.g. which differ from each other in the species or strain of fungi), based on a plurality of samples each of which belongs to one of those groups. The total number of groups is $N_G$ (>1). The number of samples per one group is $N_g$ (>1). The total number of samples is $N_s(=N_G \times N_g)$.

The mass spectrometer unit 1 performs a mass spectrometric analysis on each of the $N_s$ prepared samples to obtain mass spectrum data over a predetermined range of mass-to-charge ratios (Step S1). The mass spectrum data obtained with the mass spectrometer unit 1 are sent to the data-analyzing unit 2 and stored in the data storage section 20. It should be noted that not only mass spectra obtained with one specific mass spectrometer unit 1 but also mass spectrum data similarly obtained with other mass spectrometers can be stored in the data storage section 20. In other words, the mass spectrum data obtained for a large number of samples to be analyzed in the data-analyzing unit 2 may be data obtained with one specific mass spectrometer or those obtained with two or more different mass spectrometers. In the case of correcting the saturation characteristics of the detection output as will be described later, the mass spectrum data need to be data obtained with mass spectrometers equipped with detectors having approximately the same saturation characteristics.

In the data storage section 20, $N_s$ sets of mass spectrum data obtained for $N_s$ samples are stored. At a predetermined timing, the peak list creator 21 reads mass spectrum data from the data storage section 20 and performs a peak detection on the mass spectrum in each data set according to predetermined criteria Subsequently, the peak list creator 21 determines the mass-to-charge-ratio value and peak-intensity value of each detected peak, and creates a peak list, which is a collection of a large number of combinations of mass-to-charge-ratio values and peak-intensity values, for each mass spectrum, or for each sample (Step S2). The number of peak lists is the same as that of the samples. $N_s$.

Figures 3A, 3B:
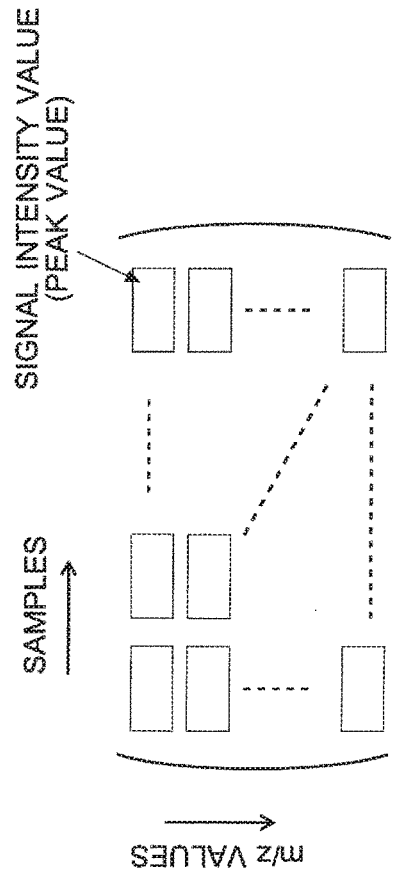
FIG. 3A is a conceptual diagram of a peak matrix.
FIG. 3B is an example of the peak matrix created based on mass spectra obtained for a plurality of samples.

Based on the $N_s$ peak lists, the peak matrix creator 22 creates a peak matrix including the peak-intensity values as its element, with the m/z values arrayed in the vertical direction and sample names in the horizontal direction (Step S3). FIG. 3A is a conceptual diagram of the peak matrix. FIG. 3B shows one example of the peak matrix. Every m/z value which is present in at least one of the peak lists is listed in the matrix. Each row of the peak matrix includes peak-intensity values in all samples for a peak which has been observed in at least one of the samples. Accordingly, the peak-intensity values in one row represent the peak-intensity distribution at one mass-to-charge ratio. To visualize the peak-intensity distribution, the peak-intensity distribution creator 23 classifies each peak-intensity value on each row of the peak matrix into one of the classes defined by dividing a range of intensity values into predetermined intervals, counts the number of peak-intensity values in each class, and creates a histogram which shows the peak-intensity distribution, i.e. the relationship between the class and number (frequency) of the peak-intensity values (Step S4). It should be noted that Step S4 may be omitted.

Subsequently, for each of the peak-intensity distributions which respectively correspond to different mass-to-charge-ratio values, i.e. for each row of the peak-intensity values in the peak matrix, the probability distribution determiner 24 performs a process for determining whether or not there is a difference between the $N_G$ groups, based on the peak-intensity distribution concerned (Step S5). A specific procedure is as follows.

Initially, based on the peak-intensity distribution corresponding to one row in the peak matrix, the mean-and-variance estimator 241 estimates the mean and variance of the distribution (Step S51). For the estimation, all peak-intensity values in the row concerned in the peak matrix may be simply used as the peak-intensity distribution, or the histogram created in Step S4 may be used.

Meanwhile, based on the saturation characteristics information of the mass spectrometer unit 1, which is previously stored in the saturation characteristics information memory 242, the saturation characteristics corrector 243 corrects the peak-intensity distribution whose mean and variance have been calculated in Step S51 (Step S52). It is often the case with a detector used in a mass spectrometer that the phenomenon of output saturation occurs, i.e. the output of the detector levels off within a high-output region in the input-output characteristics. If the lowering of the intensity value due to the saturation of the detection output is not corrected, the peak-intensity distribution will be inaccurate. Typically, output saturation characteristics of a detector can be determined by experiment or simulation. Accordingly, in the present embodiment, a characteristics function previously determined for the detector is stored in the saturation characteristics information memory 242, and the peak-intensity distribution is corrected using an inverse function of the characteristics function. Needless to say, the process of Step S52 can be omitted in the case where a detector which is free from such an output saturation is used, or in the case where a detector is used within a limited range of its input-output characteristics in which the output of the detector will not become saturated.

The distribution function tester 244 performs a hypothesis test for determining whether or not the peak-intensity distribution which has been corrected in Step S52 is in conformity to the lognormal distribution, based on the estimated values of the mean and variance calculated in Step S51 (Step S53). The reason to perform a hypothesis test for the conformity to the lognormal distribution rather than the normal distribution is because the detector of the mass spectrometer unit 1 in the present embodiment has exponential amplification characteristics. In the case where the detector in the mass spectrometer unit 1 has linear amplification characteristics, a hypothesis test for the conformity to the ordinary normal distribution rather than the lognormal distribution can be performed.

There are various techniques of the hypothesis test for normality, such as the goodness-of-fit test using a chi-square distribution, Kolmogolov-Smirnov test, Lilliefors test and Shapiro-Wilk W test. An appropriate technique can be used. As a result of the hypothesis test in Step S53, if the hypothesis that the distribution is in conformity to the lognormal distribution has not been rejected, it is possible to conclude that it is reasonable to consider that all samples at the m/z value concerned constitute one group. In other words, in such a case, it is concluded that there is no difference between the groups. By comparison, if the hypothesis has been rejected, it is concluded that a difference between the groups is likely to exist.

The distribution function tester 244 determines whether or not the test for the presence or absence of a difference between the groups by Steps S51-S53 has been completed for all rows in the peak matrix (Step S54). If there is a row which remains to be tested, the operation returns from Step S54 to Step S51. Accordingly, the test for the presence or absence of a difference between the groups is performed for all rows in the peak matrix by the repetition of Steps S51-S54. The output processor 25 selects the m/z values corresponding to the rows for which the hypothesis has been rejected by the test, i.e. the rows which have been judged as having a significant difference between the groups, as the candidates of the marker peaks and displays the result on the screen of the display unit 4 (Step S6).

As for the histograms created in Step S4, the system can be configured to display them on the screen of the display unit 4 in response to a predetermined operation performed on the input unit 3 by the user.

As described thus far, the mass spectrometer system according to the present embodiment uses information on all samples belonging to a plurality of groups to determine whether or not those samples can be considered as belonging to one group. Therefore, even in the case where the number $N_g$ of samples belonging to each group is comparatively small, the difference analysis can be performed with high accuracy if the total number $N_s$ of samples is large to a certain extent.

EXAMPLE

An actual example of the difference analysis performed in the mass spectrometer system according to the previous embodiment is hereinafter described.

In the difference analysis, a total of 272 samples ($N_s$=272) were prepared for 34 strains ($N_G$=34) of microorganisms, with eight samples ($N_g$=8) from each strain. The 272 samples were each subjected to mass spectrometry in the mass spectrometer unit 1 to obtain mass spectra A peak matrix was created from the 272 mass spectra according to Steps S2 and S3 described earlier. With each strain of microorganisms as one group, a test was performed to determine whether or not there was a difference in peak-intensity distribution between the groups.

Figure 4:
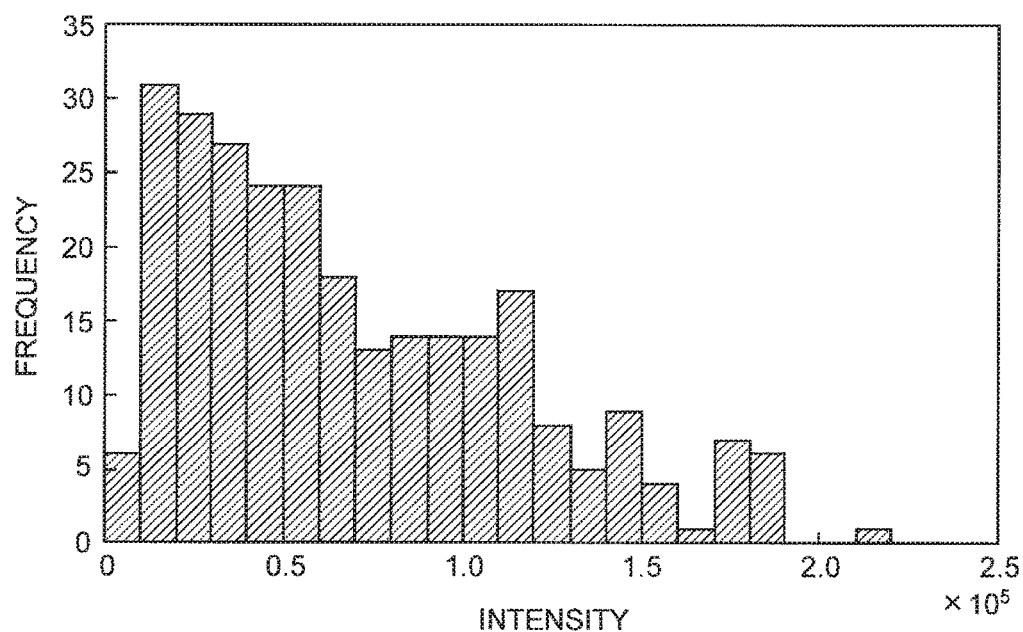
FIG. 4 is one example of the histogram created from peak-intensity values included in one row of a peak matrix.
Figure 5:
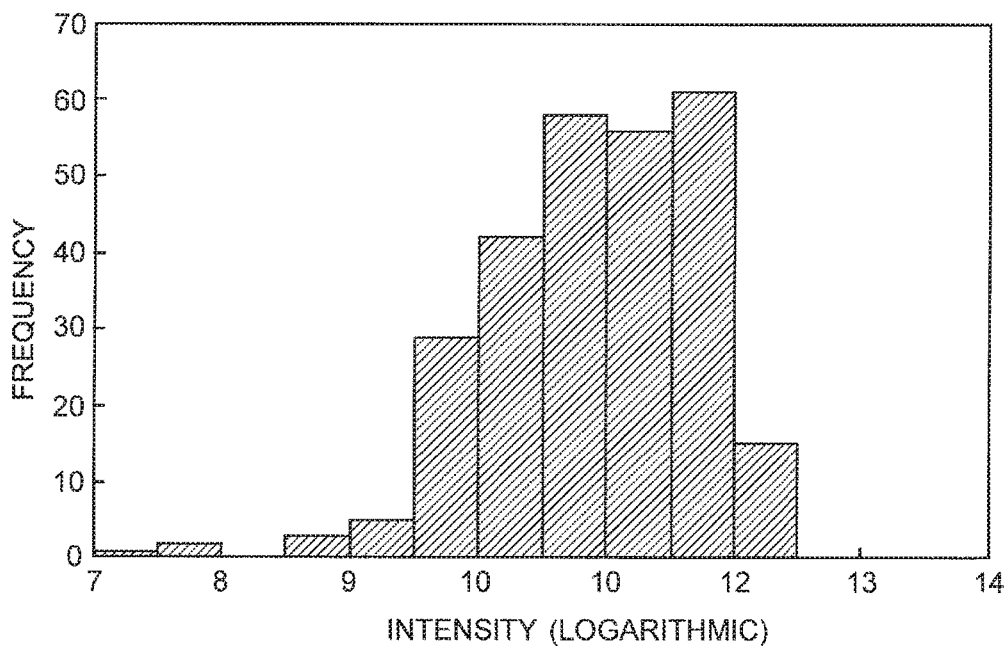
FIG. 5 is a histogram created from the same set of peak-intensity values as shown in FIG. 4, with the horizontal axis indicating the peak-intensity values on logarithmic scale.

FIG. 4 is a histogram showing a peak-intensity distribution created from one row in the peak matrix. FIG. 5 is a histogram showing the same peak-intensity distribution, with the horizontal axis indicating the peak-intensity values on logarithmic scale. For those peak-intensity distributions, whether or not there was a difference between the groups (i.e. between the strains) was analyzed as follows.

Figure 6:
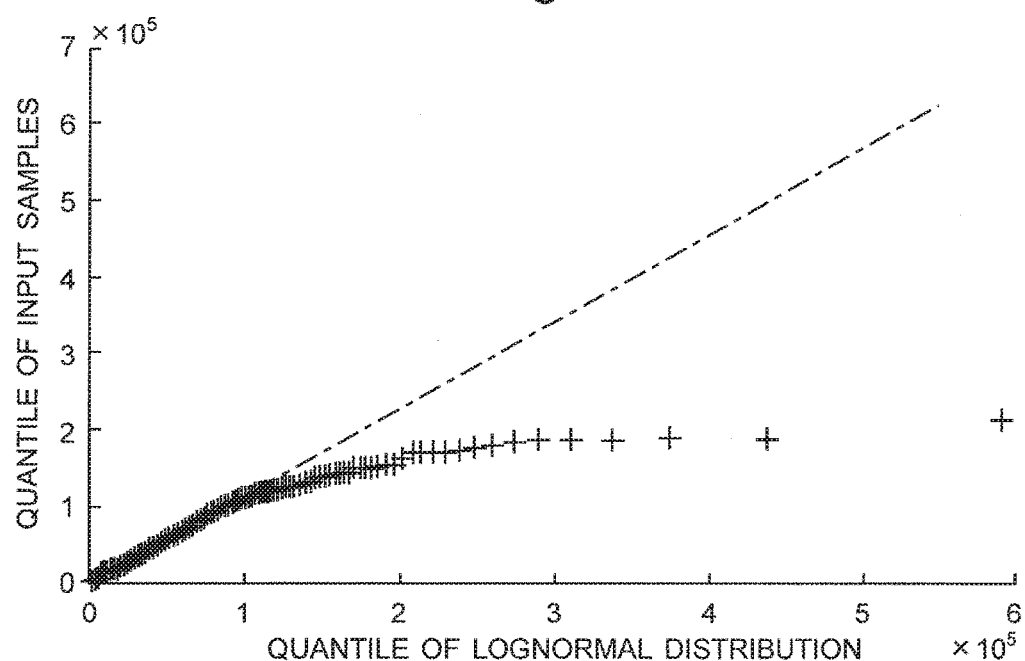
FIG. 6 is a Q-Q plot prepared on the assumption of a lognormal distribution having the mean and variance estimated from the peak-intensity distribution shown in FIG. 5.

The mean and variance values of the peak-intensity distribution shown in FIG. 4 were estimated by fitting an assumed lognormal distribution to the peak-intensity distribution. A quantile-quantile (Q-Q) plot of the peak-intensity distribution was subsequently created, using the lognormal distribution with the estimated mean and variance as the theoretical distribution. FIG. 6 shows the obtained Q-Q plot. If the peak-intensity distribution in question is a lognormal distribution, the plotted points should lie on the straight line at an angle of 45 degrees as shown by the long dashed short dashed line in FIG. 6. However, as can be seen in FIG. 6, the plotted points level off within a high-intensity region (in the right area in FIG. 6).

Such a result is likely to be due to the output saturation of the detector in the mass spectrometer unit 1. Accordingly, with reference to Non Patent Literature 2, a model which represents the relationship between an ideal output x and the actual output of the detector was created using the detector characteristics function S(x) expressed by equations (1):

$$S(x)=x \text{ (for } 0 \leq x \leq a\text{)}$$

$$S(x)=a+\{(x-a+c)^b-c^b\}\times(c^{J-b}/b)\text{(for }a<x\text{)} \quad (1)$$

where a (>0), b (<0) and c (>0) are coefficients determined by the fitting. S(x) is differentiable at x=a; S'(a)=1.

Figure 7:
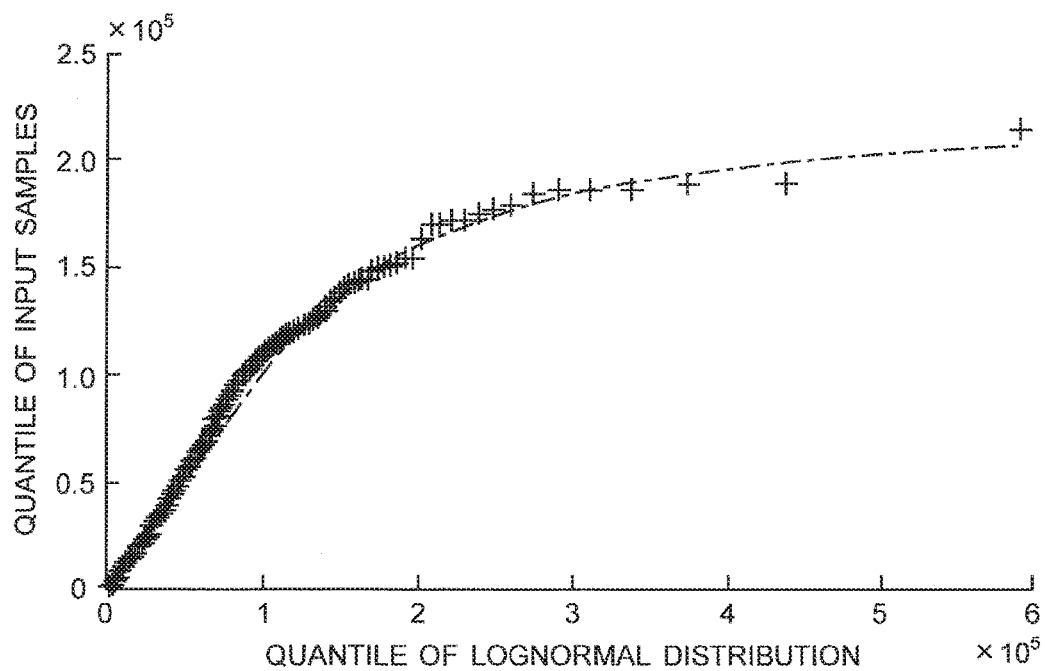
FIG. 7 is a graph showing the result of the fitting of a characteristics function, with an output saturation of a detector considered, to the Q-Q plot shown in FIG. 6.
Figure 8:
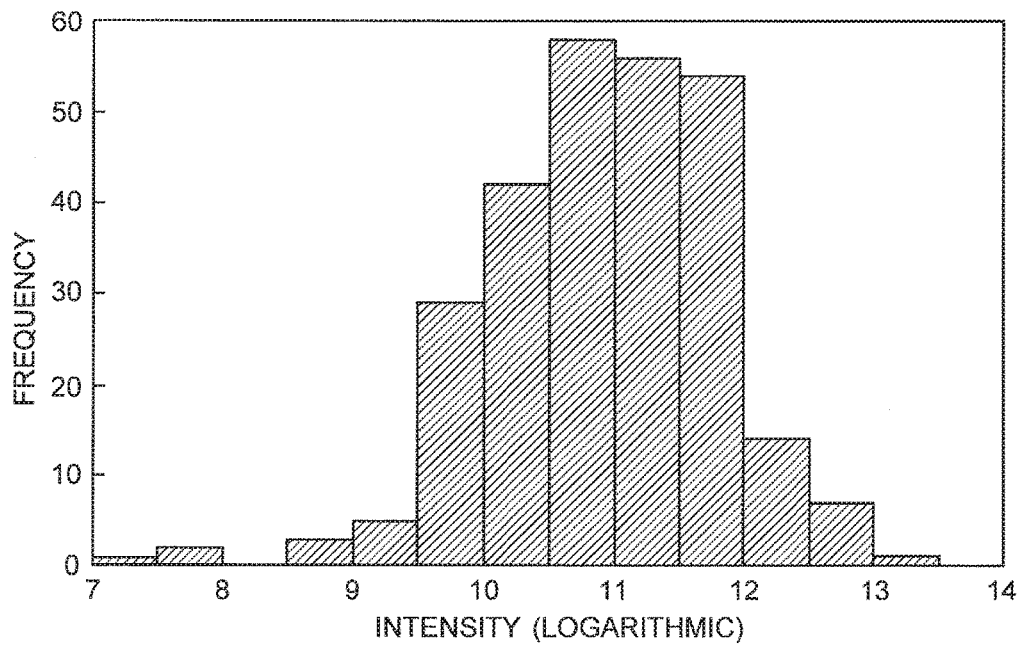
FIG. 8 is a histogram of the peak-intensity distribution after the correction of the output characteristics of the detector.

Refitting the model to the Q-Q plot shown in FIG. 6, using equations (1) in which the output saturation is considered, results in the Q-Q plot shown FIG. 7. The plots in FIG. 7 are distributed along the ideal curve indicated by the long dashed short dashed line. Accordingly, the influence of the output saturation of the detector can be reduced by correcting the peak-intensity values using the inverse function $S^{-1}(x)$ of the detector characteristics function $S(x)$ determined in this manner. FIG. 8 is a histogram created from the corrected peak-intensity distribution, with the horizontal axis indicating the peak-intensity values on logarithmic scale. The hypothesis that "this corrected peak-intensity distribution is in conformity to the lognormal distribution" was tested by Lilliefors test (see Non Patent Literature 3), and a p-value of 0.1845 was obtained.

Normally, a hypothesis with a p-value of 0.05 or smaller is rejected. In the present case, it is sufficiently certain that the hypothesis will not be rejected. Consequently, it is concluded that there is no difference between the groups at the peak (m/z value) corresponding to the aforementioned row in the peak matrix.

Figure 9:
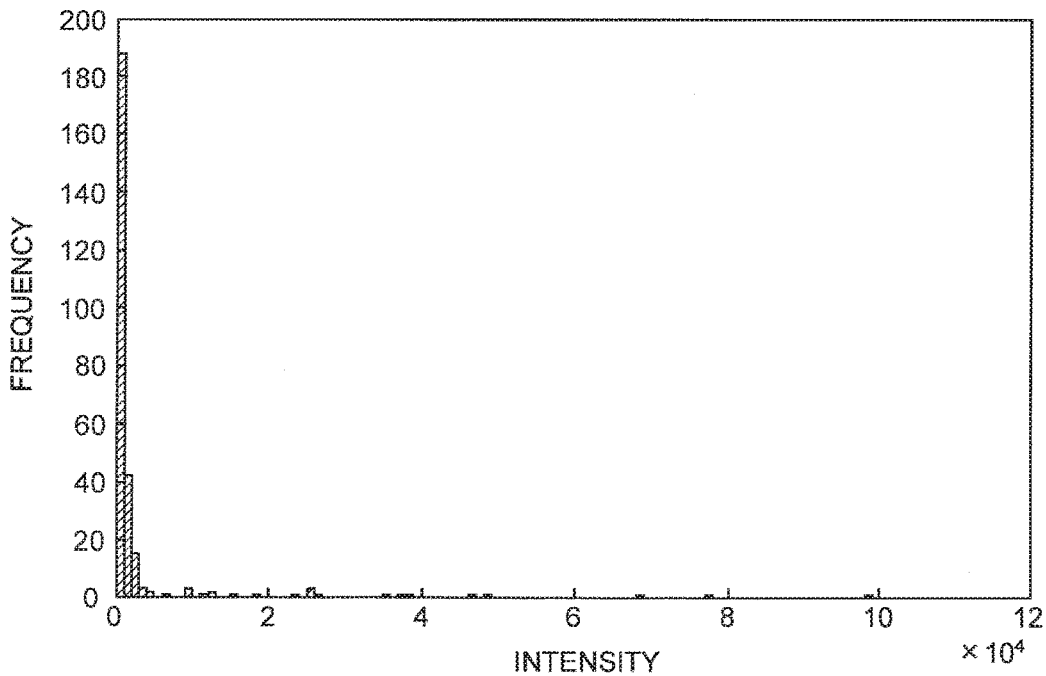
FIG. 9 is one example of the histogram created from peak-intensity values included in another row of the peak matrix.
Figure 10:
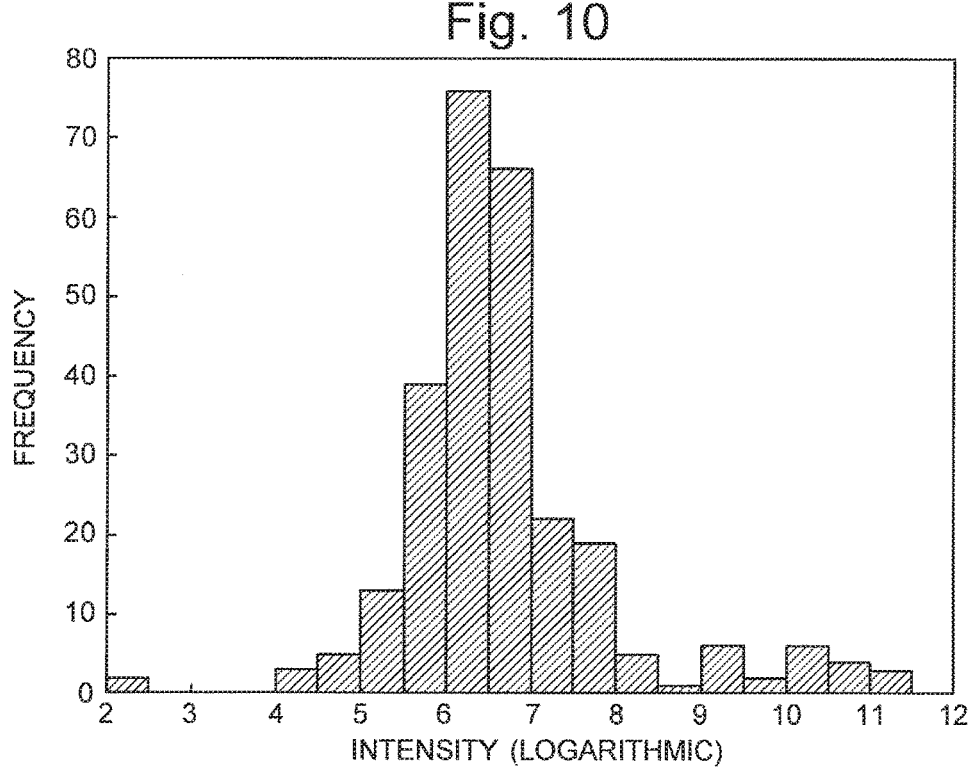
FIG. 10 is a histogram of the same set of peak-intensity values as shown in FIG. 9, with the horizontal axis indicating the peak-intensity values on logarithmic scale.

FIGS. 9 and 10 show peak-intensity distributions created from another row in the same peak matrix. FIG. 9 is a histogram with the horizontal axis simply indicating the intensity values, while FIG. 10 is a histogram with the horizontal axis indicating the intensity values on logarithmic scale. The previously described hypothesis test was similarly performed on these peak-intensity distributions.

Figure 11:
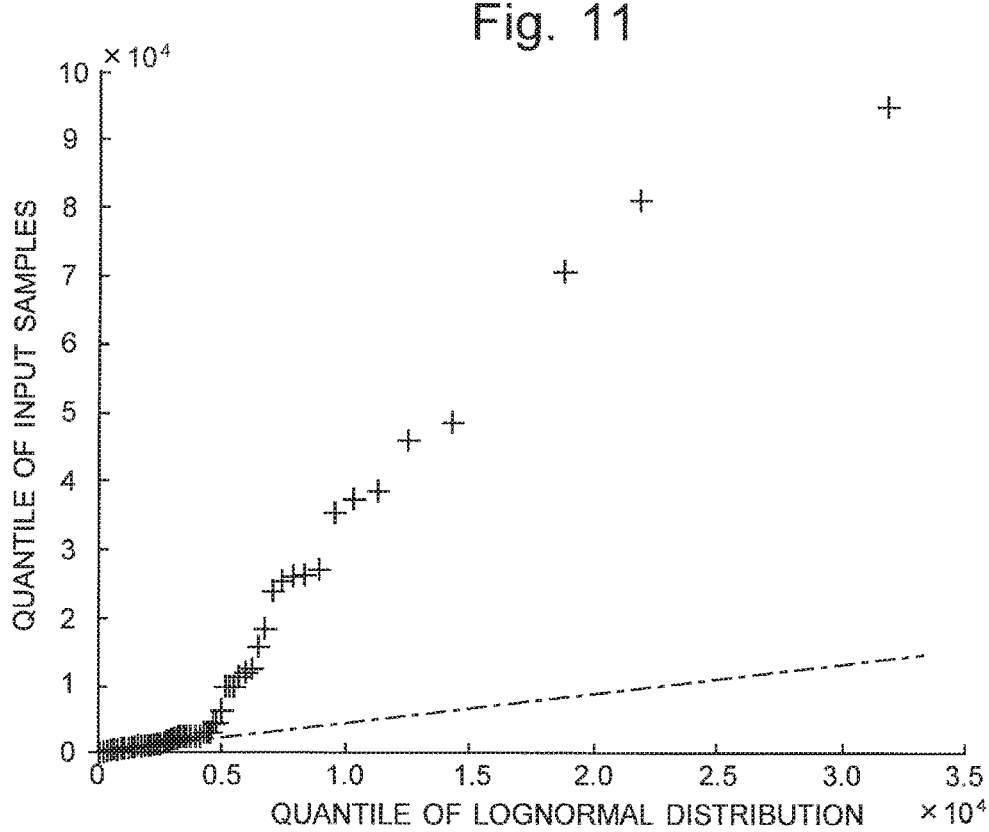
FIG. 11 is a Q-Q plot prepared on the assumption of a lognormal distribution having the mean and variance estimated from the peak-intensity distribution shown in FIG. 10.

The mean and variance were estimated from the peak-intensity distribution shown in FIG. 10. A Q-Q plot was created using the lognormal distribution having the estimated mean and variance as the assumed theoretical distribution. The result was as shown in FIG. 11. A comparison of FIG. 11 with FIG. 6 demonstrates that the relationship of the plotted points is totally different. Using equations (1) for the fitting is not appropriate in the present case. This means that correcting the output saturation characteristics will produce no substantial effect, and therefore, it is possible to consider that the corrected peak intensity is equal to the original peak intensity. Accordingly, as in the previous case, the hypothesis that "the corrected peak-intensity distribution (which equals the original peak-intensity distribution) is in conformity to the lognormal distribution" was tested by Lilliefors test. The obtained p-value was less than 0.001. The hypothesis is rejected in the present case. That is to say, it is concluded that a difference between the groups is likely to exist at the peak corresponding to the row in question in the peak matrix. Accordingly, this peak is selected as a candidate of the marker peak.

In addition, it is reasonable to consider that the peak-intensity distribution in the present case is a superposition of two peak-intensity distributions with different means and variances, as shown in FIG. 12.

As illustrated in the previous examples, with the mass spectrometer system according to the previous embodiment, whether or not there is a difference between groups can be determined for each row of the peak matrix, i.e. for each of the mass-to-charge ratios of the peaks observed in mass spectra which respectively correspond to a large number of samples. Accordingly, candidates of the marker peaks which are likely to contribute to the difference between the groups can be accurately located.

It should be noted that the previous embodiment is a mere example of the present invention, and any change, modification, addition or the like appropriately made within the spirit of the present invention will naturally fall within the scope of claims of the present application.

REFERENCE SIGNS LIST

1 . . . Mass Spectrometer Unit
2 . . . Data-Analyzing Unit
20 . . . Data Storage Section
21 . . . Peak List Creator
22 . . . Peak Matrix Creator
23 . . . Peak-Intensity Distribution Creator
24 . . . Probability Distribution Determiner
241 . . . Mean-and-Average Estimator
242 . . . Saturation Characteristics Information Memory
243 . . . Saturation Characteristics Corrector
244 . . . Distribution Function Tester
25 . . . Output Processor
3 . . . Input Unit
4 . . . Display Unit

The invention claimed is:

1. A mass spectrometric data analyzer for locating a marker peak whose expression varies among a plurality of groups of samples, based on mass spectrum data obtained by performing a mass spectrometric analysis on each of the samples each of which belongs to one of the plurality of groups, the mass spectrometric data analyzer comprising:
   a) a peak information collector for grouping peak-intensity values on mass spectra obtained for a plurality of given samples, for each mass-to-charge-ratio value at which a peak is observed on any one of the mass spectra, based on mass spectrum data obtained for the given samples; and
   b) a significant difference determiner for determining, for each mass-to-charge-ratio value, whether or not a peak-intensity distribution is in conformity to a probability distribution using a predetermined parameter, the peak-intensity distribution being either a distribution based on a plurality of peak-intensity values corresponding to one mass-to-charge-ratio value, determined by the peak information collector, or a distribution obtained by correcting the aforementioned distribution, and for selecting a mass-to-charge-ratio value giving a peak-intensity distribution which is judged to be in inconformity to the probability distribution, as a candidate of a marker peak which is considered as showing a significant difference between the plurality of groups.

2. The mass spectrometric data analyzer according to claim 1, wherein:
the probability distribution is a normal distribution or lognormal distribution, and the significant difference determiner includes:
   b1) a mean-and-variance estimator for estimating a mean and a variance from an uncorrected or corrected peak-intensity distribution; and
   b2) a statistical tester for performing a hypothesis test for a conformity of the uncorrected or corrected peak-intensity distribution to the normal distribution or lognormal distribution, based on the mean and the variance estimated by the mean-and-variance estimator.

3. The mass spectrometric data analyzer according to claim 2, wherein:
the significant difference determiner further includes a saturation characteristics corrector for correcting the peak-intensity distribution to remove an influence of output saturation characteristics of a detector in a mass spectrometer, and determines whether or not the peak-intensity distribution after correction by the saturation characteristics corrector is in conformity to the normal distribution of lognormal distribution.

4. The mass spectrometric data analyzer according to claim 3, wherein:
the saturation characteristics corrector corrects the peak-intensity distribution using an inverse function of a previously determined detector characteristics function.

5. The mass spectrometric data analyzer according to claim 1, wherein:
the peak information collector includes:
a1) a peak detector for detecting a peak on each of given mass spectra obtained for a plurality of samples; and
a2) a peak matrix creator for creating a peak matrix based on information concerning the peaks detected in each mass spectrum, the peak matrix including peak-intensity values arrayed as elements, with the mass-to-charge-ratio values of the peaks assigned to columns or rows, and information for identifying the samples assigned to rows or columns, and
the significant difference determiner creates a peak-intensity distribution for each row or column in which peak-intensity values corresponding to a same mass-to-charge-ratio value are arrayed in the peak matrix.

6. A non-transitory computer readable medium recording a program for analyzing mass spectrometric data using a computer, to locate a marker peak whose expression varies among a plurality of groups of samples, based on mass spectrum data obtained by performing a mass spectrometric analysis on each of the samples each of which belongs to one of the plurality of groups, wherein the program makes the computer perform following steps:
a) a peak information collection step in which peak-intensity values on mass spectra obtained for a plurality of given samples are grouped for each mass-to-charge-ratio value at which a peak is observed on any one of the mass spectra, based on mass spectrum data obtained for the given samples; and
b) a significant difference determination step in which, for each mass-to-charge-ratio value, whether or not a peak-intensity distribution is in conformity to a probability distribution using a predetermined parameter is determined, the peak-intensity distribution being either a distribution based on a plurality of peak-intensity values corresponding to one mass-to-charge-ratio value, determined in the peak information collection step, or a distribution obtained by correcting the aforementioned distribution, and a mass-to-charge-ratio value giving a peak-intensity distribution which is judged to be in inconformity to the probability distribution is selected as a candidate of a marker peak which is considered as showing a significant difference between the plurality of groups.

7. The non-transitory computer readable medium recording a program for analyzing mass spectrometric data according to claim 6, wherein:
the probability distribution is a normal distribution or lognormal distribution, and the significant difference determination step includes estimating a mean and a variance from an uncorrected or corrected peak-intensity distribution and performing a hypothesis test for a conformity of the uncorrected or corrected peak-intensity distribution to the normal distribution or lognormal distribution, based on the estimated mean and variance.

8. The non-transitory computer readable medium recording a program for analyzing mass spectrometric data according to claim 7, wherein:
the significant difference determination step further includes a saturation characteristics correction step in which the peak-intensity distribution is corrected to remove an influence of output saturation characteristics of a detector in a mass spectrometer, and determines whether or not the peak-intensity distribution after correction is in conformity to the normal distribution of lognormal distribution.

9. The non-transitory computer readable medium recording a program for analyzing mass spectrometric data according to claim 8, wherein:
the saturation characteristics correction step includes correcting the peak-intensity distribution using an inverse function of a detector characteristics function previously determined for removing an influence of output saturation characteristics of a detector.

10. The non-transitory computer readable medium recording a program for analyzing mass spectrometric data according to claim 6, wherein:
the peak information collection step includes:
a1) a peak detection step in which a peak is detected on each of given mass spectra obtained for a plurality of samples; and
a2) a peak matrix creation step in which a peak matrix is created based on information concerning the peaks detected in each mass spectrum, the peak matrix including peak-intensity values arrayed as elements, with the mass-to-charge-ratio values of the peaks assigned to columns or rows, and information for identifying the samples assigned to rows or columns, and
the significant difference determination step includes creating a peak-intensity distribution for each row or column in which peak-intensity values corresponding to a same mass-to-charge-ratio value are arrayed in the peak matrix.

* * * * *